(12) United States Patent
Otaki et al.

(10) Patent No.: US 11,096,592 B2
(45) Date of Patent: Aug. 24, 2021

(54) SENSOR MODULE AND BIOLOGICAL INFORMATION DISPLAY SYSTEM

(71) Applicants: ALPS ALPINE CO., LTD., Tokyo (JP); Genial Light CO., LTD., Shizuoka (JP)

(72) Inventors: Yukio Otaki, Miyagi (JP); Toshio Kawano, Miyagi (JP); Naoki Ito, Miyagi (JP); Ryo Shimokita, Shizuoka (JP)

(73) Assignees: ALPS ALPINE CO., LTD., Tokyo (JP); Genial Light CO., LTD., Shizuoka (JP)

(*) Notice: Subject to any disclaimer, the term of this patent is extended or adjusted under 35 U.S.C. 154(b) by 330 days.

(21) Appl. No.: 16/437,104

(22) Filed: Jun. 11, 2019

(65) Prior Publication Data
US 2019/0290135 A1    Sep. 26, 2019

Related U.S. Application Data (63) Continuation of application No. PCT/JP2017/045256, filed on Dec. 18, 2017.

(30) Foreign Application Priority Data

Dec. 27, 2016  (JP) .............................. JP2016-253871

(51) Int. Cl.
*A61B 5/1455* (2006.01)
*A61B 5/0205* (2006.01)
(Continued)

(52) U.S. Cl.
CPC .......... *A61B 5/0205* (2013.01); *A61B 5/0245* (2013.01); *A61B 5/1455* (2013.01);
(Continued)

(58) Field of Classification Search
CPC . A61B 5/0205; A61B 5/1455; A61B 5/14551; A61B 5/14552; A61B 5/0245;
(Continued)

(56) References Cited

U.S. PATENT DOCUMENTS 5,746,697 A    5/1998  Swedlow et al.
6,912,413 B2 *  6/2005  Rantala .............. A61B 5/14551
                                                     600/322

(Continued)

FOREIGN PATENT DOCUMENTS

JP    H04-332536    11/1992
JP    H07-265284    10/1995
(Continued)

OTHER PUBLICATIONS

International Search Report for PCT/JP2017/045256 dated Mar. 20, 2018.
Japanese Office Action for 2018-559063 dated Mar. 10, 2020.

*Primary Examiner* — Chu Chuan Liu
(74) *Attorney, Agent, or Firm* — IPUSA, PLLC (57) ABSTRACT

A sensor module includes a light emitter that emits light beams including near-infrared light beams towards a subject; a light receiver that receives light beams having passed through the subject; and a controller that estimates biological information based on signals output from the light receiver. The light emitter includes a plurality of light emitting elements that emit near-infrared light beams having central wavelengths different from each other. The light emitter produces sets of light emissions by causing the plurality of light emitting elements to sequentially and intermittently emit the near-infrared light beams. In given two consecutive sets of light emissions produced by the light emitter, a second non-light-emission period of time T4 is longer than a first non-light-emission period of time T2. The controller estimates the biological information in a process- (Continued)

ing period of time T41 that is set in correspondence with the second non-light-emission period of time T4.

7 Claims, 7 Drawing Sheets

(51) Int. Cl.
*A61B 5/0245* (2006.01)
*A61B 5/024* (2006.01)
*A61B 5/00* (2006.01)

(52) U.S. Cl.
CPC ...... *A61B 5/14551* (2013.01); *A61B 5/02416* (2013.01); *A61B 5/742* (2013.01); *A61B 2560/0209* (2013.01)

(58) Field of Classification Search
CPC ....... A61B 5/742; A61B 5/02416; A61B 5/72; A61B 5/7203
See application file for complete search history.

(56) References Cited

U.S. PATENT DOCUMENTS

| | | | |
|---|---|---|---|
| 7,190,985 B2* | 3/2007 | Petersen | A61B 5/14551 600/322 |
| 2003/0158486 A1 | 8/2003 | Nakashima et al. | |
| 2014/0243626 A1* | 8/2014 | Krishnan | A61B 5/14552 600/323 |
| 2016/0135692 A1 | 5/2016 | Lisogurski et al. | |
| 2016/0278712 A1 | 9/2016 | Sagara et al. | |

FOREIGN PATENT DOCUMENTS

| | | |
|---|---|---|
| JP | 2000-504599 | 4/2000 |
| JP | 2000-325330 | 11/2000 |
| JP | 2003-153882 | 5/2003 |
| JP | 2003-240716 | 8/2003 |
| JP | 2008-188216 | 8/2008 |
| JP | 2015-198702 | 11/2015 |
| JP | 2016-2167 | 1/2016 |
| JP | 2016-189924 | 11/2016 |
| WO | 2014045346 | 3/2014 |

* cited by examiner

SENSOR MODULE AND BIOLOGICAL INFORMATION DISPLAY SYSTEM

CROSS-REFERENCE TO RELATED APPLICATIONS

This application is a continuation of International Application No. PCT/JP2017/045256 filed on Dec. 18, 2017 and designating the U.S., which claims priority to Japanese Patent Application No. 2016-253871 filed on Dec. 27, 2016. The contents of these applications are incorporated herein by reference in their entirety.

BACKGROUND OF THE INVENTION

1. Field of the Invention

The disclosures herein relate to a sensor module for estimation of biological information that emits light including near-infrared light towards a subject, receives light that has passed through the subject, and generates a signal corresponding to near-infrared light included in the received light, and relate to a biological information display system that includes the sensor module.

2. Description of the Related Art

Patent Document 1 describes a blood component measuring apparatus that measures blood components of an arterial blood in a living organism. The blood component measuring apparatus described in Patent Document 1 includes a light amount detecting unit, a dark level detecting unit, a pulse rate detecting unit, a calculating unit, and a blood component measuring unit. The light amount detecting unit causes a light emitting unit to periodically emit light to a living organism at a first timing, and causes a light detecting unit to detect a light amount measurement value of light transmitted through the living organism. The dark level detecting unit causes the light detecting unit to detect a dark level measurement value at a second timing without causing the light emitting unit to emit light. The calculating unit calculates a time difference value with respect to two light amount measurement values detected at time intervals in accordance with the pulse rate. The blood component measuring unit measures blood components of the arterial blood based on the light amount measurement values, the dark level measurement value, and the time difference value.

In the blood component measuring apparatus described in Patent Document 1, an interval of time between the first timing and the second timing (i.e., a measurement cycle) is set to a cycle (⅟50 seconds or ⅟60 seconds) of the commercial frequency (50 Hz or 60 Hz), and the measurement cycle is constant. Further, in order to measure blood components of the arterial blood, the blood component measuring units use a light amount measurement value of red light, a light amount measurement value of infrared light, and a dark level measurement value, which are measured in the constant measurement cycle. Namely, the blood component measuring unit measures blood components of the arterial blood when measurement values, measured in the constant measurement cycle, are all obtained.

For sensor modules that measure biological information such as blood oxygen saturation (blood oxygen concentration) and biological information display systems, it is desired to reduce power consumption. One effective way to reduce the power consumption of such a sensor module and a biological information display system is to decrease the clock frequency of a central processing unit (CPU) of the sensor module.

However, if the clock frequency of the CPU is decreased in a case where blood components of an arterial blood are measured when measurement values measured in constant periods are all obtained as in the blood component measuring apparatus described in Patent Document 1, there may be a possibility that a process for measuring blood components overlaps with the next process such as a process for emitting light or measuring light that has passed through a living organism. If a process for measuring blood components overlaps with the next process such as a process for emitting light or measuring light, the sensor module may fail to operate properly.

RELATED-ART DOCUMENTS

Patent Documents

[Patent Document 1] Japanese Laid-Open Patent Publication No. 2003-153882

SUMMARY OF THE INVENTION

It is a general object of the present invention to provide a sensor module and a biological information display system that reduces power consumption.

According to at least one embodiment, a sensor module includes a light emitter configured to emit light beams including near-infrared light beams towards a subject, a light receiver configured to receive light beams that have passed through the subject, and a controller configured to estimate biological information based on signals output from the light receiver. The light emitter includes a plurality of first light emitting elements disposed spaced apart from each other and configured to emit near-infrared light beams having central wavelengths different from each other. The light receiver includes a light receiving element that is disposed to receive the near-infrared light beams emitted from the plurality of first light emitting elements and that is sensitive to the near-infrared light beams. The light emitter produces sets of light emissions by causing the plurality of first light emitting elements to sequentially and intermittently emit the near-infrared light beams, and, in given two consecutive sets of light emissions produced by the light emitter, a second non-light-emission period of time is longer than a first non-light-emission period of time, the first non-light-emission period of time being a non-light-emission period of time occurring between two consecutive light emission periods of time in each of the given two consecutive sets of light emissions, and the second non-light-emission period of time being a non-light-emission period of time occurring between a light emission period of time that occurs last in a first set of light emissions of the given two consecutive sets of light emissions and a light emission period of time that occurs first in a latter set of light emissions of the given two consecutive sets of light emissions. The controller estimates the biological information in a processing period of time that is set in correspondence with the second non-light-emission period of time.

BRIEF DESCRIPTION OF THE DRAWINGS

Other objects and further features of the present invention will be apparent from the following detailed description when read in conjunction with the accompanying drawings, in which.

DESCRIPTION OF THE PREFERRED EMBODIMENTS

In the following, embodiments of the present invention will be described with reference to the accompanying drawings. In the drawings, the same elements are denoted by the same reference numerals, and a detailed description thereof will be omitted as appropriate. The terms "top" and "bottom" are used to conveniently describe a relative positional relationship between each member, and are not intended to indicate an absolute positional relationship.

As used herein, the term "set of light emissions" refers to a set of light emissions in which a light emitter causes a plurality of light emitting elements to sequentially and intermittently emit light. The term "set of light emissions" includes a light emission period of time in which one of the plurality of light emitting elements emits light, a non-light-emission period of time that continues from the above light emission period of time and in which the plurality of light emitting elements stop emitting light, and a light emission period of time that continues from the above non-light-emission period of time and in which another one of the plurality of light emitting elements emits light. Accordingly, the term "set of light emissions" is defined as a period of time from the start of a light emission period of time in which the first light emission is performed until the end of a light emission period of time in which the last light emission is performed. Herein, a non-light-emission period of time included in a set of light emissions is referred to as a "first non-light-emission period of time". As described above, a set of light emissions is repeatedly performed. Herein, a non-light-emission period of time continuing from a light emission period of time that occurs last in a first set of light emissions of two consecutive sets of light emissions ends when a light emission period of time that occurs first in the latter set of light emissions of the two consecutive sets of light emissions is started. The above-described non-light-emission period of time occurring between the two consecutive sets of light emissions is referred to as a "second non-light-emission period of time".

A controller can start a process for estimating biological information (an estimation process), only after a set of light emissions is completed by the light emitter, light beams reach a light receiving element through a subject, signals are output from the light receiver based on the light beams received by a light receiving element, and the signals are all input into the controller. Therefore, the estimation process can be performed only in a second non-light-emission period of time. The light emitter of a sensor module with the above-described configuration causes the plurality of light emitting elements to intermittently emit light beams at emission timings as described above. Thus, the length of the second non-light-emission period of time is longer than the length of the first non-light-emission period of time. If light is emitted three or more times in a set of light emissions, the set of light emissions includes a plurality of first non-light-emission periods of time. In such a case, the plurality of first non-light-emission periods of time may have the same length or may have different lengths. If the plurality of first non-light-emission periods of time have different lengths, it may be preferable to set the length of the second non-light-emission period of time longer than the longest first non-light-emission period time of the plurality of first non-light-emission periods of time.

By setting the lengths of the non-light-emission periods of time as described above, the length of a processing period of time of the controller, which is set in correspondence with the second non-light-emission period of time, can be sufficiently secured. Thus, it becomes possible to constantly avoid a situation in which before the above-described estimation process is completed, the first light emission in the next set of light emissions is started and the time at which to start a process (such as an analog-to-digital conversion process) based on the light emission in the next set is reached. The possibility of occurrence of the above situation would become high if the clock frequency of the controller is decreased and thus processing time of the controller becomes longer. However, according to the sensor module with the above-described configuration, even in such a situation, it is possible for the controller to complete estimation of biological information before the processing period of time of the controller, which is set in correspondence with the second non-light-emission period of time, ends. Accordingly, in the sensor module with the above-described configuration, it is possible to reduce the power consumption of the sensor module by decreasing the clock frequency of the controller while maintaining a measurement cycle.

Figure 1:
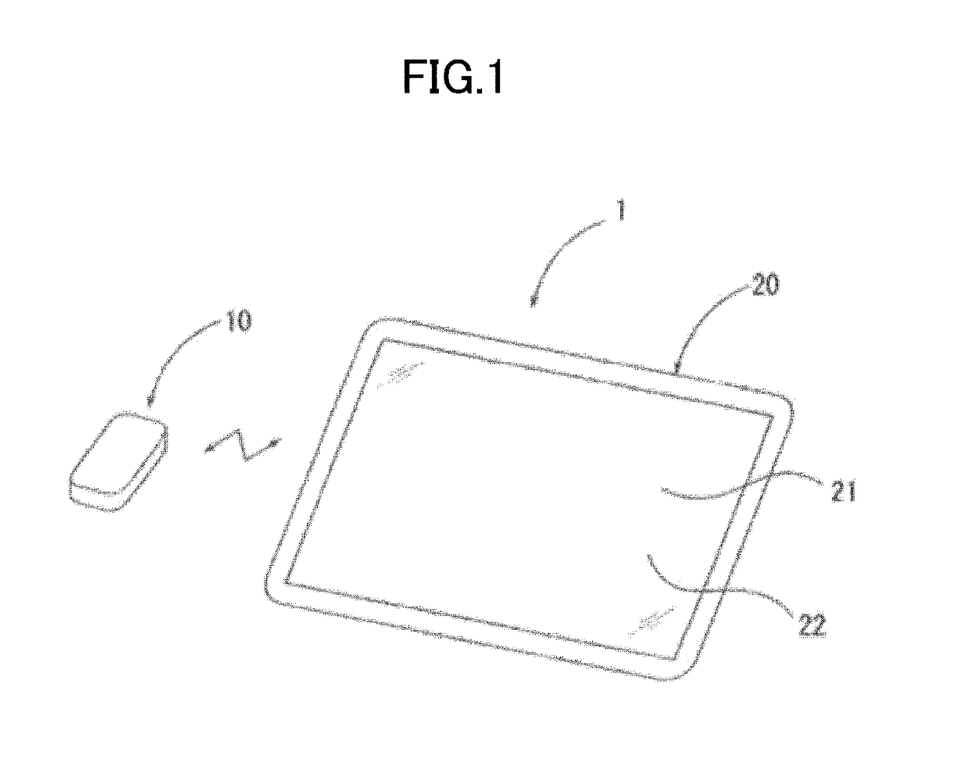
FIG. 1 is a perspective view of a biological information display system according to an embodiment of the present invention.
Figure 2:
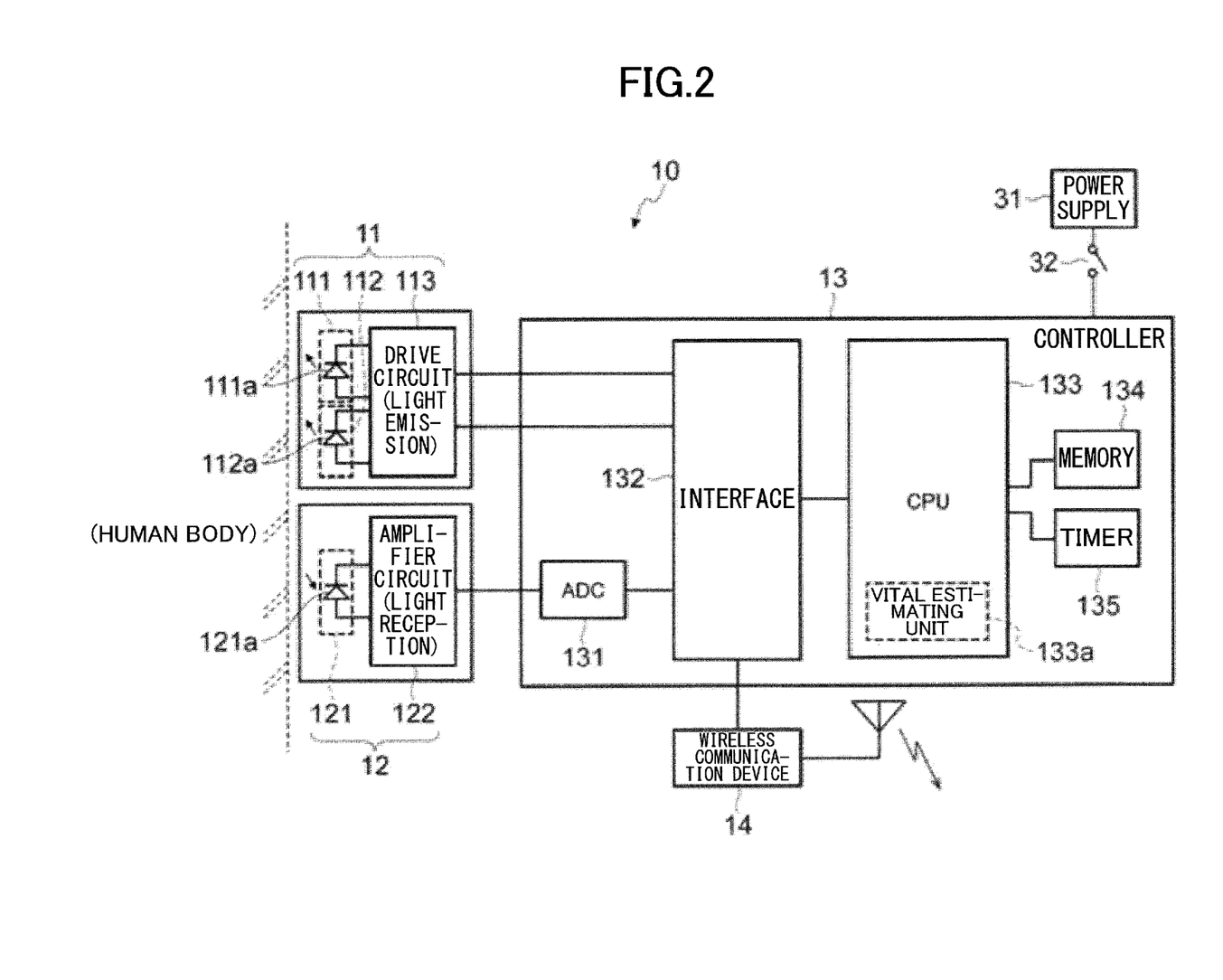
FIG. 2 is a functional block diagram of a sensor module included in the biological information display system of FIG. 1.
Figure 3:
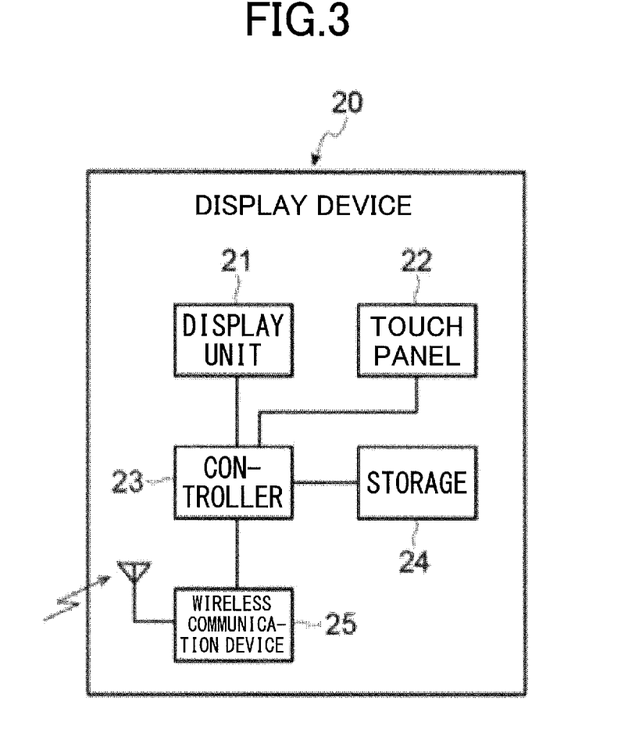
FIG. 3 is a functional block diagram of a display device included in the biological information display system of FIG. 1.
Figure 4:
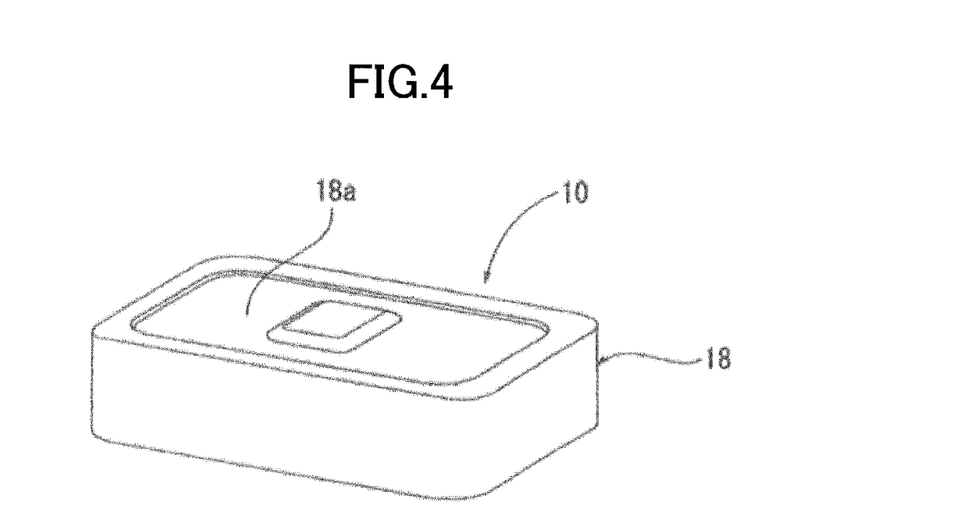
FIG. 4 is a perspective view of the sensor module included in the biological information display system of FIG. 1.
Figure 5:
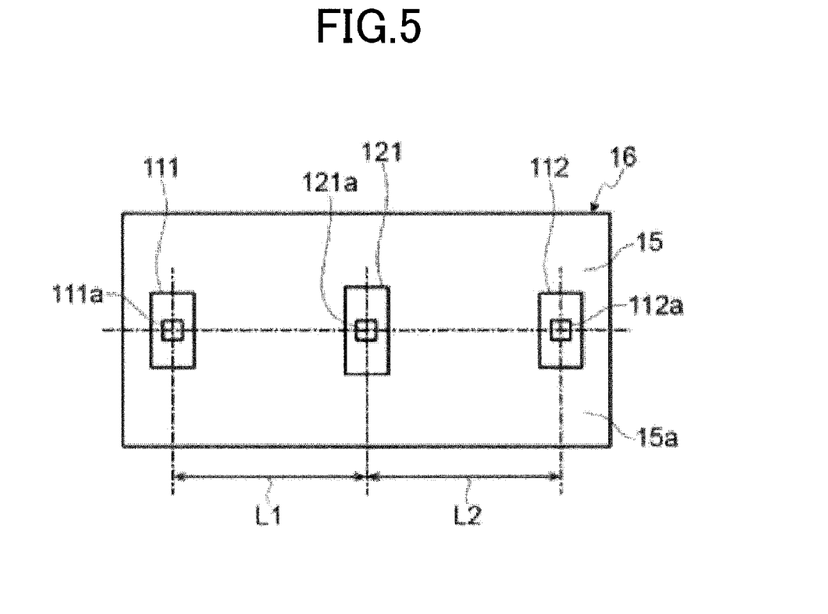
FIG. 5 is a plan view of a substrate unit included in the sensor module of FIG. 4.

FIG. 1 is a perspective view of a biological information display system according to an embodiment of the present invention. FIG. 2 is a functional block diagram of a sensor module included in the biological information display system illustrated in FIG. 1. FIG. 3 is a functional block diagram of a display device included in the biological information display system illustrated in FIG. 1. FIG. 4 is a perspective view of the sensor module included in the biological information display system illustrated in FIG. 1. FIG. 5 is a plan view of a substrate unit included in the sensor module illustrated in FIG. 4.

A biological information display system 1 according to the present embodiment illustrated in FIG. 1 includes a portable sensor module 10 that is attached by, for example, a rubber band to be directly in contact with the arm, the chest, or any other body part of a subject (a living organism), estimates biological information on the subject, and transmits the estimated biological information through wireless communication. The biological information display system 1 further includes a display device 20 that displays biological information transmitted from the sensor module 10.

As illustrated in FIG. 2 through FIG. 5, the sensor module 10 includes a light emitter 11, a light receiver 12, a controller 13, a wireless communication device 14, a substrate unit 16 that includes a substrate 15 on which the above components are mounted, and a case 18 that houses the substrate unit 16. Further, the sensor module 10 includes a power source circuit (not illustrated) for implementing a battery operation.

The light emitter 11 includes a first light emitting element package 111, a second light emitting element package 112, and a drive circuit 113. The first light emitting element package 111 includes, within one package, a light emitting element 111a such as a light-emitting diode element or a laser element that emits light including near-infrared light. The second light emitting element package 112 includes, within one package, a light emitting element 112a such as a light-emitting diode element or a laser element that emits light including near-infrared light. The drive circuit 113 drives the light emitting element 111a included in the first light emitting element package 111 and the light emitting element 112a included in the second light emitting element package 112.

The light emitting element 111a, which is one of a "plurality of light emitting elements", is able to emit near-infrared light that has a wavelength shorter than 805 nm as a central wavelength (a first central wavelength $\lambda 1$). Further, the light emitting element 112a, which is another one of the "plurality of light emitting elements", is able to emit near-infrared light that has a wavelength longer than 805 nm as a different central wavelength (a second central wavelength $\lambda 2$). Note that 805 nm is a wavelength that is less affected by absorption due to water, which accounts for most of a living organism (a subject). In other words, 805 nm is a wavelength of an isosbestic point at which an absorption coefficient of deoxygenated hemoglobin and an absorption coefficient of oxygenated hemoglobin are equal to each other. By using wavelengths of around 805 nm to observe a difference between absorbances of hemoglobin in the body, it is possible to estimate biological information with high accuracy. As used herein, the term central wavelength of near-infrared light refers to a wavelength at which the intensity of light (energy of light) is the highest within a wavelength range of near-infrared light emitted by a light emitting element.

In the present embodiment, the light emitting element 111a of the first light emitting element package 111 can emit near-infrared light having a first central wavelength $\lambda 1$ of 760 nm. The light emitting element 112 of the second light emitting element package 112 can emit near-infrared light having a second central wavelength $\lambda 2$ of 850 nm. However, the central wavelengths are not limited thereto. The first central wavelength $\lambda 1$ of near-infrared light emitted from the light emitting element 111a is preferably shorter than 805 nm, and the second central wavelength $\lambda 2$ of near-infrared light emitted from the light emitting element 112a is preferably longer than 805 nm. For example, the first central wavelength $\lambda 1$ may be 780 nm, and the second central wavelength $\lambda 2$ may be 830 nm. Further, the first central wavelength $\lambda 1$ may be 640 nm, and the second central wavelength $\lambda 2$ may be 940 nm. Preferably, the wavelength range of near-infrared light emitted from the light emitting element 111a may be 760±50 nm, and the wavelength range of near-infrared light emitted from the light emitting element 112a may be 850±50 nm. More preferably, the wavelength range of near-infrared light emitted from the light emitting element 111a may be 760±20 nm, and the wavelength range of near-infrared light emitted from the light emitting element 112a may be 850±20 nm. With the above configuration, the output of the light receiver 12 becomes larger, thus increasing the signal to noise (S/N) ratio.

The light receiver 12 includes a light receiving element package 121 and an amplifier circuit 122. The light receiving element package 121 includes, within one package, a light receiving element 121a that outputs signals (light reception signals) corresponding to received near-infrared light. The amplifier circuit 122 amplifies the light reception signals output from the light receiving element 121a of the light receiving element package 121.

The light receiving element 121a, which is a "light receiving element", is disposed to receive light beams emitted from the light emitting element 111a and the light emitting element 112a, and is sensitive to near-infrared light having a wavelength close to the first central wavelength $\lambda 1$ and near-infrared light having a wavelength close to the second central wavelength $\lambda 2$. Specifically, the light receiving element 121a is disposed on the upper surface 15a of the substrate 15, which will be described later, between the light emitting element 111a and the light emitting element 112a, and receives light beams emitted from the light emitting element 111a and the light emitting element 112a.

The controller 13 is configured by a microcomputer, and includes an analog-to-digital converter (ADC) 131, an interface 132, a central processing unit (CPU) 133 that includes a vital estimating unit 133a, a memory 134, and a timer 135. The controller 13 causes the CPU 133 to execute various programs stored in the memory 134.

The CPU 133 uses a timer IC included in the timer 135 to transmit timing signals to the drive circuit 113 of the light emitter 11 via the output of the interface, and controls the drive circuit 113 such that the first light emitting element package 111 and the second light emitting element package 112 of the light emitter 11 emit near-infrared light. More specifically, the CPU 133 causes the light emitting element 111a of the first light emitting element package 111 to emit near-infrared light having the first central wavelength $\lambda 1$, and to stop emitting the near-infrared light after a predetermined period of time has elapsed. Further, the CPU 133 causes the light emitting element 112a of the second light emitting element package 112 to emit near-infrared light having the second central wavelength $\lambda 2$, and to stop emitting the near-infrared light after a predetermined period of time has elapsed. The CPU 133 causes near-infrared light having the central wavelength $\lambda 1$ and the near-infrared light having the central wavelength $\lambda 2$ to be emitted intermittently and alternately.

Further, the controller 13 uses the ADC 131 to convert amplified light reception signals output from the amplifier circuit 122 of the light receiver 12 into processable digital signal information (signal output values). Based on the signal information converted by the ADC 131 and received via the input of the interface 132, the CPU 133 causes the vital estimating unit 133a to estimate biological information such as changes in blood hemoglobin, changes in blood oxygen level, and a pulse rate. The controller 13 functions as a biological information estimating unit that estimates biological information based on signals output from the light receiver 12.

The wireless communication device 14 is configured by a wireless communication IC. The wireless communication device 14 transmits biological information estimated by the controller 13 to the display device 20, which will be described later, through communication using a wireless communication standard such as Bluetooth (registered trademark), for example. It should be noted that the sensor module 10 may be configured to transmit, instead of biological information, the above-described signal information used to estimate biological information to the display device 20 through wireless communication, and to estimate biological information based on the signal information in the display device 20.

The substrate 15 is a printed circuit board on which a wiring pattern formed of a copper foil is formed on a glass epoxy substrate. As illustrated in FIG. 5, the first light emitting element package 111 including the first light emitting element package 111, the second light emitting element package 112 including the light emitting element 112a, and the light receiving element package 121 including the light receiving element 121a are mounted on the upper surface 15a of the substrate 15. The light emitting element 111a and the light emitting element 112a are arranged on the upper surface 15a while being spaced apart from each other. The light receiving element 121a is arranged at an intermediate position between the light emitting element 111a and the light emitting element 112a. The light emitting element 111a, the light emitting element 112a, and the light receiving element 121a are arranged in one straight line.

In the present embodiment, an interval L1 between the light emitting element 111a and the light receiving element 121a and an interval L2 between the light emitting element 112a and the light receiving element 121a are each set to 4 mm. The interval L1 and the interval L2 are preferably from 4 to 11 mm. Further, the interval L1 and the interval L2 are preferably the same. The drive circuit 113 of the light emitter 11, the amplifier circuit 122 of the light receiver 12, a microcomputer constituting the controller 13, and the wireless communication IC constituting the wireless communication device 14 are mounted on the lower surface (not illustrated) of the substrate 15.

As illustrated in FIG. 4, the case 18 is formed in a hollow box shape, an top wall 18a of the case 18 is formed of a material having translucency, and parts other than the top wall 18a of the case 18 are formed of a material having a light-blocking property. The case 18 houses the substrate unit 16 such that the upper surface 15a of the substrate 15 faces the top wall 18a of the case 18. The case 18 is attached to the subject such that the top wall 18a is in contact with the surface of the subject (the skin of the human). In this way, the light emitting element 111a of the first light emitting element package 111, the light emitting element 112a of the second light emitting element package 112, and the light receiving element 121a of the light receiving element package 121 are disposed facing the surface of the subject via the top wall 18a.

The display device 20 is a tablet terminal and executes various types of application programs (hereinafter simply referred to as "applications") such as pre-installed applications and applications downloaded from the Internet. The display device 20 functions as any type of device by executing an application according to the purpose. In the present embodiment, the display device 20 functions as a device constituting a part of the biological information display system 1 by executing an application for displaying biological information.

As illustrated in FIG. 3, the display device 20 includes a display unit 21 configured by a liquid crystal display, a touch panel 22 stacked on the surface of the liquid crystal display, a controller 23 including a microcomputer, a storage including a working memory and a memory for information storage, and a wireless communication device 25 configured by a wireless communication module.

The display unit 21 displays various screens for displaying documents and images in accordance with display control information output from the controller 23, and displays operation items such as buttons, text input fields, keyboards, and numeric keypads on the various screens.

When a touch operation is performed on the touch panel 22 by a user at a position corresponding to any of the above-described operation items, the touch panel 22 outputs a signal corresponding to the touch operation to the controller 23.

For example, when information related to a touch operation performed on the touch panel 22 by a user is input into the controller 23, the controller 23 outputs, to the display unit 21, display control information for displaying a predetermined image, based on the input information. Further, various types of information are transmitted and received between the controller 23 and the storage 24. The controller 23 reads predetermined information from the storage 24, and causes the storage 24 to store predetermined information. The wireless communication device 25 receives biological information transmitted from the sensor module 10. The controller 23 loads the biological information received by the wireless communication device 25.

In the present embodiment, the display device 20 executes an application program for displaying biological information (hereinafter simply referred to as a "biological application") that serves as a biological information displaying program for displaying biological information transmitted from the sensor module 10.

In the biological information display system 1, the sensor module 10 starts a biological information estimating operation when a power supply 31 is turned on via a power supply switch 32. In the biological information estimating operation, the sensor module 10 causes the light emitter 11 to emit near-infrared light, causes the light receiver 12 to receive near-infrared light that has passed through the subject, estimates biological information such as changes in blood hemoglobin, changes in blood oxygen level, and a pulse rate based on the received near-infrared light, and successively transmits the biological information to the display device 20. The display device 20 causes the controller 23 to execute the biological application to display, on the display unit 21, the biological information transmitted from the sensor module 10.

More specifically, biological information is estimated as follows. In response to the reception of a control signal from the controller 13, the drive circuit 113 causes the light emitting element 111a, which emits near-infrared light having the first central wavelength $\lambda 1$ of 760 nm, and the light emitting element 112a, which emits near-infrared light having the second central wavelength $\lambda 2$ of 850 nm, to alternately emit light beams towards the subject at predetermined timings. In other words, the CPU 133 transmits timing signals to the drive circuit 113, such that a near-infrared light beam having the first central wavelength $\lambda 1$ of 760 nm and a near-infrared light beam having the second central wavelength $\lambda 2$ of 850 nm are sequentially and intermittently emitted from the light emitting element 111a and the light emitting element 112a.

Then, the light receiving element 121a receives weak light beams reflected by the subject, and outputs signals corresponding to the received reflected light beams. The signals output from the light receiving element 121a are amplified by the amplifier circuit 122, and are input into the controller 13. The controller 13 causes the ADC 131 to convert the input signals from analog to digital, and obtains signal output values for the respective wavelengths (760 nm and 850 nm). Data such as a calculation formula and a table indicating a relationship between signal output values and biological information values is preliminarily stored in, for example, the memory 134 of the controller 13. By referring to the above data, biological information corresponding to signal output values can be obtained. In this way, the controller 13 calculates biological information after receiving a signal corresponding to reflected light of near-infrared light having the first central wavelength λ1 of 760 nm and a signal corresponding to reflected light of near-infrared light having the second central wavelength λ2 of 850 nm. Details of the biological information estimating operation according to the present embodiment will be described later.

Figure 6:
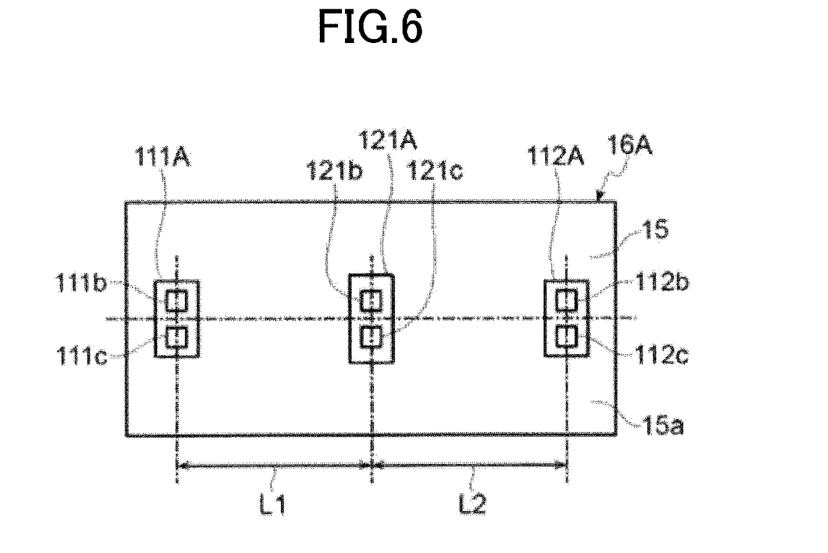
FIG. 6 is a plan view of a substrate unit included in a sensor module according to a variation of the embodiment.

FIG. 6 is a plan view of a substrate unit included in a sensor module according to a variation of the present embodiment. A substrate unit 16A of the sensor module according to the variation further includes a plurality of light emitting elements and a plurality of additional light emitting elements.

The plurality of additional light emitting elements emit near-infrared light having central wavelengths that are the same as those of the plurality of light emitting elements. More specifically, a first light emitting element package 111A includes, within one package, a first light emitting element 111b and a second light emitting element 111c that are each formed of a light-emitting diode element or a laser element that emits near-infrared light. A second light emitting element package 112A includes, within one package, a first light emitting element 112b and a second light emitting element 112c that are each formed of a light-emitting diode element or a laser element that emits near-infrared light.

The drive circuit 113 drives the first light emitting element 111b and the second light emitting element 111c of the first light emitting element package 111A, and the first light emitting element 112b and the second light emitting element 112c of the second light emitting element package 112A.

The first light emitting element 111b, which is one of the "plurality of light emitting elements", is able to emit near-infrared light that has a wavelength shorter than 805 nm as a central wavelength (a first central wavelength λ1). Further, the second light emitting element 111c, which is another one of the "plurality of light emitting elements", is able to emit near-infrared light that has a wavelength longer than 805 nm as a different central wavelength (a second central wavelength λ2).

The first light emitting element 112b, which is one of the "plurality of additional light emitting elements", is able to emit near-infrared light that has the wavelength shorter than 805 nm as the central wavelength (the first central wavelength λ1). Namely, the first light emitting element 112b of the second light emitting element package 112A emits near-infrared light having the same central wavelength as the first central wavelength λ1 of near-infrared light emitted from the first light emitting element 111b of the first light emitting element package 111A. The second light emitting element 112c, which is another one of the "plurality of additional light emitting elements", is able to emit near-infrared light that has the wavelength longer than 805 nm as the central wavelength (the second central wavelength λ2). Namely, the second light emitting element 112c of the second light emitting element package 112A emits near-infrared light having the same central wavelength as the second central wavelength λ2 of near-infrared light emitted from the second light emitting element 111c of the first light emitting element package 111A.

In the present variation, the first light emitting element 111b and the first light emitting element 112b form a pair, and are able to emit near-infrared light having the first central wavelength λ1 of 760 nm. The second light emitting element 111c and the second light emitting element 112c form a pair, and are able to emit near-infrared light having the second central wavelength λ2 of 850 nm. However, the central wavelengths are not limited thereto. The first central wavelength λ1 of near-infrared light emitted from each of the first light emitting element 111b and the first light emitting element 112b is preferably shorter than 805 nm, and the second central wavelength λ2 of near-infrared light emitted from each of the second light emitting element 111c and the second light emitting element 112c is preferably longer than 805 nm. For example, the first central wavelength λ1 may be 780 nm, and the second central wavelength λ2 may be 830 nm. Further, the first central wavelength λ1 may be 640 nm, and the second central wavelength λ2 may be 940 nm. Preferably, the wavelength range of near-infrared light emitted from each of the first light emitting element 111b and the first light emitting element 112b may be 760±50 nm, and the wavelength range of near-infrared light emitted from each of the second light emitting element 111c and the second light emitting element 112c may be 850±50 nm. More preferably, the wavelength range of near-infrared light emitted from each of the first light emitting element 111b and the first light emitting element 112b may be 760±20 nm, and the wavelength range of near-infrared light emitted from each of the second light emitting element 111c and the second light emitting element 112c may be 850±20 nm. With the above configuration, the output of the light receiver 12 becomes larger, thus increasing the signal to noise (S/N) ratio.

The light receiving element package 121A according to the variation includes, within one package, a first light receiving element 121b and a second light receiving element 121c that output signals (light reception signals) corresponding to received near-infrared light. The amplifier circuit 122 amplifies the light reception signals output from the first light receiving element 121b and the second light receiving element 121c of the light receiving element package 121.

The receiving sensitivity of the first light receiving element 121b becomes maximum at the first central wavelength λ1 of near-infrared light emitted from the first light emitting element 111b and the first light emitting element 112b. The first light receiving element 121b is sensitive to near-infrared light having a wavelength close to the first central wavelength λ1. Further, the receiving sensitivity of the second light receiving element 121c becomes maximum at the second central wavelength λ2 of near-infrared light emitted from the second light emitting element 111c and the second light emitting element 112c. The second light receiving element 121c is sensitive to near-infrared light having a wavelength close to the second central wavelength λ2. In the present variation, the receiving sensitivity of the first light receiving element 121b becomes maximum at a wavelength of 760 nm, and is able to receive near-infrared light having a wavelength range of 760±50 nm. Further, the receiving sensitivity of the second light receiving element 121c becomes maximum at a wavelength of 850 nm, and is able to receive near-infrared light having a wavelength range of 850±50 nm. It is preferable to select a light receiving element whose receiving sensitivity becomes maximum at a central wavelength of light emitted by a light emitting element.

The first light receiving element 121b is disposed on the upper surface 15a of the substrate 15 between the first light emitting element 111b and the first light emitting element 112b to receive light beams emitted from the first light emitting element 111b and the first light emitting element 112b. In addition, the second light receiving element 121c is disposed on the upper surface 15a of the substrate 15 between the second light emitting element 111c and the second light emitting element 112c to receive light beams emitted from the second light emitting element 111c and the second light emitting element 112c.

In the variation, the CPU 133 causes the first light emitting element 111b and the first light emitting element 112b to simultaneously emit near-infrared light beams having the first central wavelength λ1, and to stop emitting the near-infrared light beams after a predetermined period of time has elapsed. Namely, timings at which the first light emitting element 111b and the first light emitting element 112b emit light beams are synchronized with each other. Further, the CPU 133 causes the second light emitting element 111c and the second light emitting element 112c to simultaneously emit near-infrared light beams having the second central wavelength λ2, and to stop emitting the near-infrared light beams after a predetermined period of time has elapsed. Namely, timings at which the second light emitting element 111c and the second light emitting element 112c emit light beams are synchronized with each other. Further, The CPU 133 causes near-infrared light having the central wavelength λ1 and the near-infrared light having the central wavelength λ2 to be emitted intermittently and alternately.

According to the variation, biological information is estimated as follows. In response to the reception of a control signal from the controller 13, the drive circuit 113 causes the first light emitting element 111b and the first light emitting element 112b, which emit near-infrared light beams having the first central wavelength λ1 of 760 nm, and the second light emitting element 111c and the second light emitting element 112c, which emit near-infrared light beams having the second central wavelength λ2 of 850 nm, to alternately emit light beams towards the subject at predetermined timings. In other words, the CPU 133 transmits timing signals to the drive circuit 113, such that near-infrared light beams having the first central wavelength λ1 of 760 nm and near-infrared light beams having the second central wavelength λ2 of 850 nm are sequentially and intermittently emitted from the first light emitting element 111b and the first light emitting element 112b and the second light emitting element 111c and the second light emitting element 112c.

Then, the first light receiving element 121b and the second light receiving element 121c receive weak light beams reflected by the subject. Signals output from the first light receiving element 121b and the second light receiving element 121c are amplified by the amplifier circuit 122, and are input into the controller 13. The controller 13 causes the ADC 131 to convert the input signals from analog to digital, and obtains signal output values for the respective wavelengths (760 nm and 850 nm). Other configurations and operations are as described above with reference to FIG. 1 through FIG. 5.

According to the variation, the light emitting elements and the additional light emitting elements that emit near-infrared light having the central wavelengths are provided. More specifically, the first light emitting element 111b and the first light emitting element 112b that emit near-infrared light having the first central wavelength λ1 are provided. In addition, the second light emitting element 111c and the second light emitting element 112c that emit near-infrared light having the second central wavelength λ2 are provided. Thus, the light receiver 12 can obtain higher detection sensitivity. Accordingly, the controller 13 can estimate biological information with higher precision, even if an artery is located deeper below the skin of the subject, for example.

Next, details of the biological information estimating operation will be described with reference to the drawings. In the following description, an example in which the sensor module includes the substrate unit 16 described above with reference to FIG. 5 will be described.

Figure 7A:
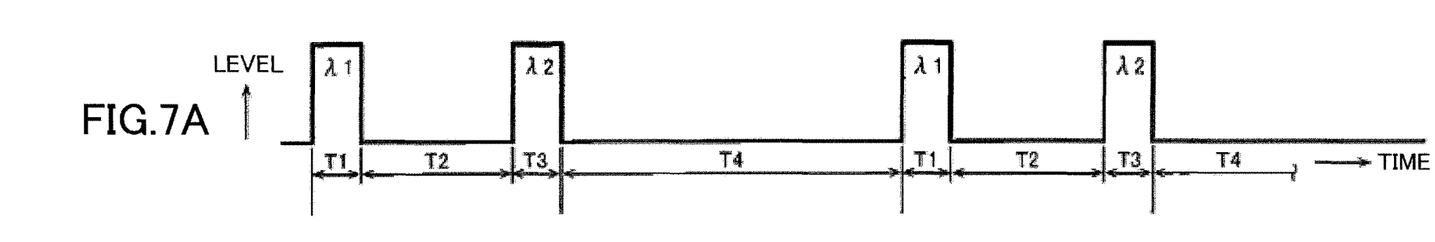
FIGS. 7A through 7D are timing diagrams illustrating a biological information estimating operation according to the embodiment.
Figure 7B:
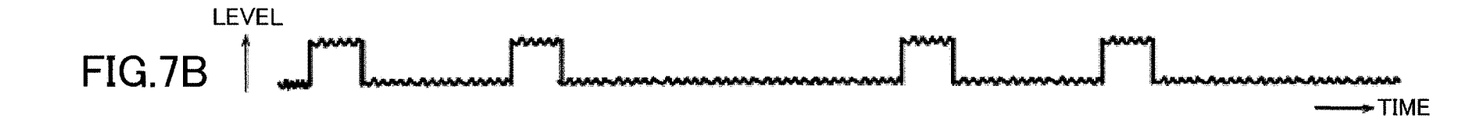
Figure 7C:
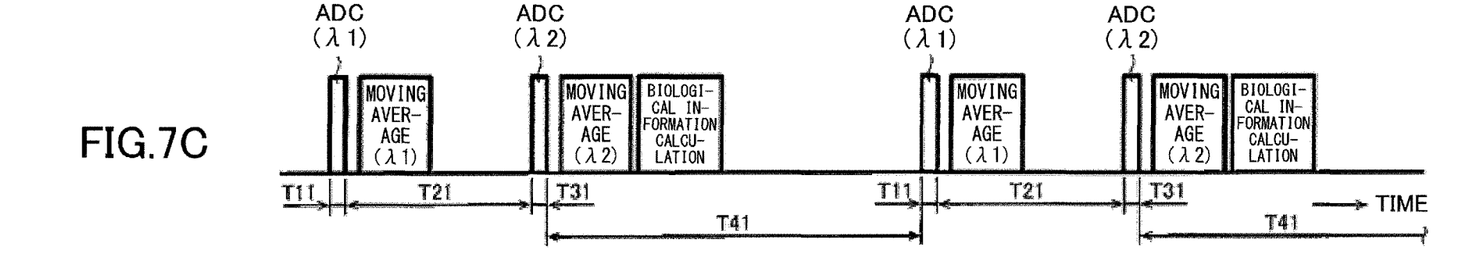
Figure 7D:
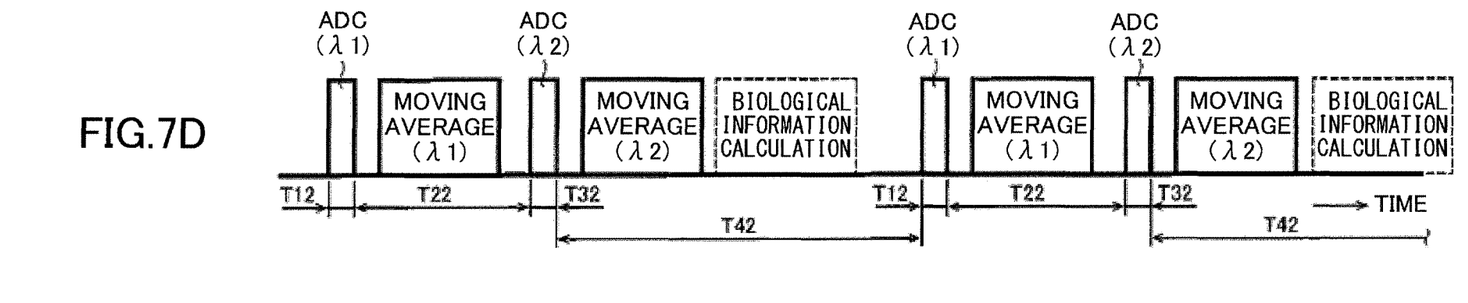
Figure 8A:
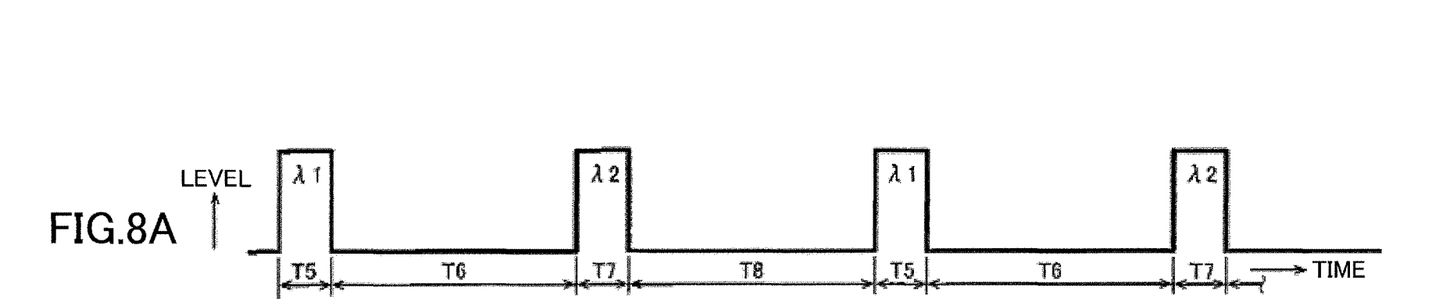
FIGS. 8A through 8D are timing diagrams illustrating a biological information estimating operation according to a comparative example.
Figure 8B:
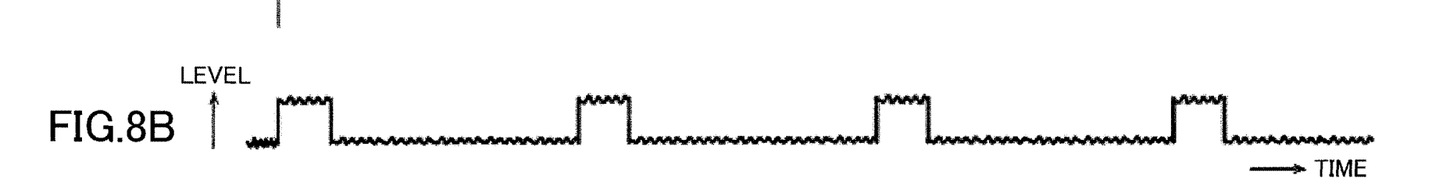
Figure 8C:
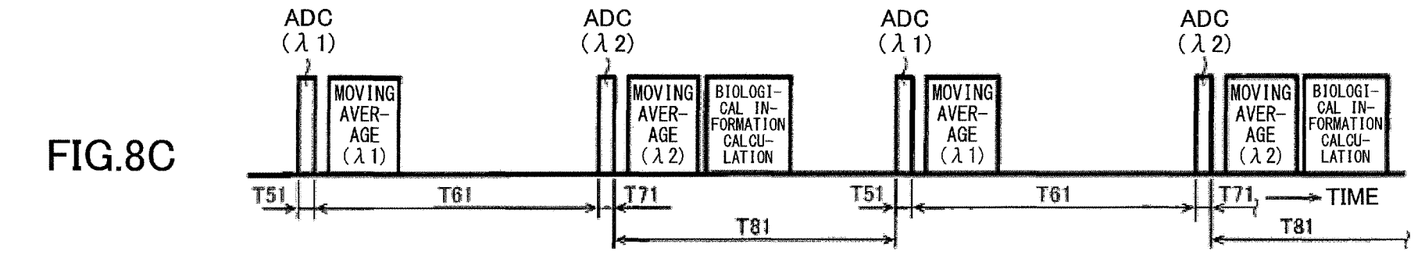
Figure 8D:
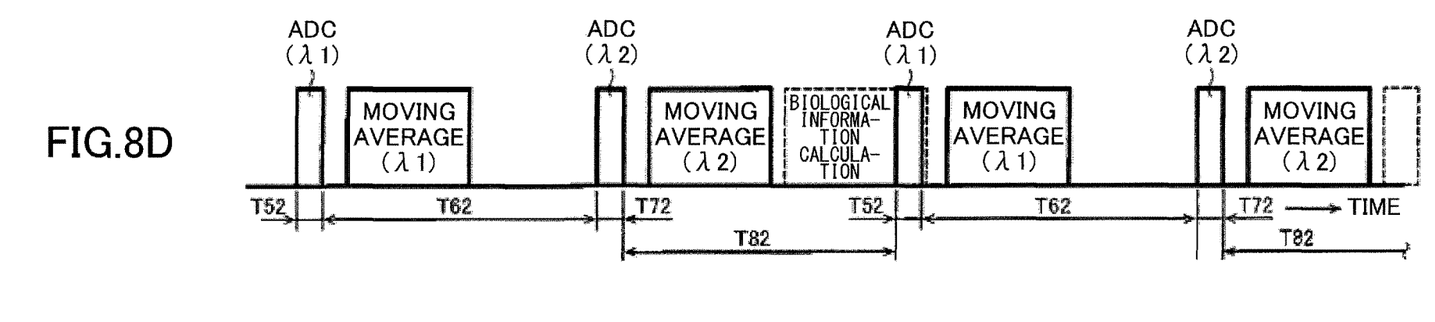

FIGS. 7A through 7D are timing diagrams illustrating the biological information estimating operation according to the embodiment. FIGS. 8A through 8D are timing diagrams illustrating a biological information estimating operation according to a comparative example. FIG. 7A and FIG. 8A each represent the level of timing signals (light emission signals) transmitted from the controller to a light emitter. FIG. 7B and FIG. 8B each represent the level of light reception signals that have been amplified and output from the light receiver. FIG. 7C and FIG. 8C each represent timings at which a controller performs processes. FIG. 7D and FIG. 8D each represent an example in which the clock frequency of a CPU is reduced as compared to the example of FIG. 7C and FIG. 8C. In FIG. 7A through FIG. 8D, the horizontal axis of each of the timing diagrams represents time.

First, a comparative example illustrated in FIGS. 8A through 8D will be described. As illustrated in FIGS. 8A through 8D, a controller intermittently and alternately emits near-infrared light having the first central wavelength λ1 and near-infrared light having the second central wavelength λ2. In other words, the controller sequentially and intermittently emits near-infrared light having the first central wavelength λ1 and near-infrared light having the second central wavelength λ2 from two light emitting elements. As illustrated in FIG. 8B, a light receiver outputs light reception signals corresponding to near-infrared light having the first central wavelength λ1 that has passed through the subject and a light reception signal corresponding to near-infrared light having the second central wavelength λ2 that has passed through the subject. Namely, the controller receives signals, corresponding to reflected light having the first central wavelength λ1 and corresponding to reflected light having the second central wavelength λ2, at respective timings corresponding to light emission signals for near-infrared light having the first central wavelength λ1 and for near-infrared light having the second central wavelength λ2.

In the comparative example, a light emission period of time T5 in which near-infrared light having the first central wavelength λ1 is emitted has the same length as that of a light emission period of time T7 in which near-infrared light having the second central wavelength λ2 is emitted. Further, a first non-light-emission period of time T6 is a non-light-emission period of time occurring between a light emission period of time T5 and a light emission period of time T7 that are two consecutive light emission periods of time in a set of light emissions. A second non-light-emission period of time T8 is a non-light-emission period of time occurring between a light emission period of time T7 that occurs last in a first set of light emissions of any two consecutive sets of light emissions and a light emission period of time T5 that occurs first in the latter set of light emissions of the two consecutive sets of light emissions. The length of the first non-light-emission period of time T6 and the length of the second non-light-emission period of time T8 are the same. Namely, a light emission cycle (T5+T6+T7+T8) of near-infrared light having the first central wavelength λ1 is the same as a light emission cycle (T7+T8+T5+T6) of near-infrared light having the second central wavelength λ2. For example, the light emission cycle (T5+T6+T7+T8) of near-infrared light having the first central wavelength λ1 and the light emission cycle (T7+T8+T5+T6) of near-infrared light having the second central wavelength λ2 may be each approximately 2 milliseconds (ms). The light emission cycle corresponds to a measurement cycle of the sensor module.

As illustrated in FIG. 8C, the length of a period of time T51 required for an analog-to-digital conversion (A/D conversion) process for converting a signal corresponding to near-infrared light having the first central wavelength λ1 is the same as the length of a period of time T71 required for the A/D conversion process for converting a signal corresponding to near-infrared light having the second central wavelength λ2. Further, the length of a period of time T61 occurring between the period of time T51 and the period of time T71 and in which the A/D conversion process is stopped is the same as the length of a period of time T81 occurring between the period of time T71 and the next period of time T51 and in which the A/D conversion process is stopped. Namely, an A/D conversion cycle (T51+T61+T71+T81) of near-infrared light having the first central wavelength λ1 is the same as an A/D conversion cycle (T71+T81+T51+T61) of near-infrared light having the second central wavelength λ2.

Then, the controller performs a moving average process for averaging a signal output from the light receiver on a per-same-central-wavelength basis, each time a light receiving element receives light emitted from a light emitting element of a plurality of light emitting elements. More specifically, in the period of time T61 (also referred to as a "processing period of time" in which processes other than A/D conversion can be performed) after A/D conversion of a signal corresponding to near-infrared light having the first central wavelength λ1 ends until the next A/D conversion of a signal corresponding to near-infrared light having the second central wavelength λ2 starts, the controller performs the moving average process for averaging the signal corresponding to the near-infrared light having the first central wavelength λ1. Further, in the time period of time (processing period of time) T81 after A/D conversion of the signal corresponding to the near-infrared light having the second central wavelength λ2 ends until the next A/D conversion of a signal corresponding to near-infrared light having the first central wavelength λ1 starts, the controller performs the moving average process for averaging the signal corresponding to the near-infrared light having the second central wavelength λ2.

Next, the controller causes the vital estimating unit of the CPU to perform a process for estimating biological information (an estimation process) after obtaining both signals generated by the moving average process performed for the near-infrared light having the first center wavelength λ1 and the near-infrared light having the second center wavelength λ2. Namely, in the processing period of time T81 set in correspondence with the second non-light-emission period of time T8, the controller causes the vital estimating unit of the CPU to perform the estimation process after obtaining all signals generated by the moving average processes performed for the near-infrared light beams having the center wavelengths emitted from the light emitters. As described above, only the moving average process is performed in the processing period of time T61 set in correspondence with the first non-light-emission period of time T6, while the moving average process and the estimation process are performed in the processing period of time T81 set in correspondence with the second non-light-emission period of time T8.

As illustrated in FIG. 8D, if the clock frequency of the CPU is decreased, the time required to perform each process increases while power consumption can be reduced. Specifically, a period of time T52 required for A/D conversion of a signal corresponding to near-infrared light having the first central wavelength λ1 becomes longer than the period of time T51 illustrated in FIG. 8C. In addition, a period of time T72 required for A/D conversion of a signal corresponding to near-infrared light having the second central wavelength λ2 becomes longer than the period of time T71 illustrated in FIG. 8C. Meanwhile, even if the clock frequency of the CPU is decreased, the light emission cycle of near-infrared light having the first central wavelength λ1 and the light emission cycle of near-infrared light having the second central wavelength λ2 do not change. Therefore, a processing period of time T62 set in correspondence with the first non-light-emission period of time T6 becomes shorter than the processing period of time T61 illustrated in FIG. 8C. In addition, a processing period of time T82 set in correspondence with the second non-light-emission period of time T8 becomes shorter than the processing period of time T81 illustrated in FIG. 8C. Further, when the clock frequency of the CPU is decreased, the time required for the moving average process and the time required for the estimation process both increase. Therefore, as indicated by a dash line of FIG. 8D, the estimation process fails to be completed by the end of the processing period of time T82, and reaches the next processing period of time T52 in which A-D conversion of a signal corresponding to near-infrared light having the first central wavelength λ1 is to be performed. In such a case, the A-D conversion would not be properly performed, thus causing the sensor module to fail to operate properly. Thus, the clock frequency of the CPU can only be decreased in such a manner that processes do not overlap. In order to avoid an overlap of processes, it is required to make the measurement cycle longer.

In light of the above, in the sensor module 10 according to the present embodiment, the second non-light-emission period of time is longer than the first non-light-emission period of time. Further, the controller 13 estimates biological information in the processing period of time set in correspondence with the second non-light-emission period of time.

Namely, as illustrated in FIG. 7A, the light emitter 11 intermittently emits near-infrared light having the first central wavelength λ1 and near-infrared light having the second central wavelength λ2, based on signals output from the controller 13, and repeatedly performs a set of light emissions. Specifically, a set of light emissions includes a light emission period of time T1 in which near-infrared light having the first central wavelength λ1 is emitted from the light emitting element 111a, a first non-light-emission period of time T2 in which any light emission is stopped, and a light emission period of time T3 in which near-infrared light having the second central wavelength λ2 is emitted from the light emitting element 112a. After the above set of light emissions is completed, any light emission is stopped in a second non-light-emission period of time T4. After the second non-light-emission period of time T4 has elapsed, the light emitter 11 starts the next set of light emissions by causing the light emitting element 111a to emit light. The cycle of repetition of a set of light emissions corresponds to a measurement cycle of the sensor module 10.

Basic time settings including the measurement cycle are similar to those of the sensor module according to the comparative example illustrated in FIG. 8. However, in the sensor module 10 according to the present embodiment, the second non-light-emission period of time T4 is set longer than the first non-light-emission period of time T2. Thus, as illustrated in FIG. 7C, a processing period of time T41 set in correspondence with the second non-light-emission period of time T4 becomes longer than a processing period of time T21 set in correspondence with the first non-light-emission period of time T2. Accordingly, when the estimation process is performed by the vital estimating unit 133a of the CPU 133 in addition to the moving average process in the processing period of time T41, these processes can be completed before reaching a period of time T11 in which A/D conversion of a signal is performed based on the first light emission of the next set of light emissions.

As illustrated in FIG. 7D, the time required to perform each process increases when the clock frequency of the CPU 133 is lowered. However, as in the example of FIG. 7C in which the clock frequency of the CPU is not lowered, it is possible to complete the moving average process and the estimation process in a processing period of time T42, which is set in correspondence with the second non-light-emission period of time T4, before reaching a period of time T12 in which A/D conversion of a signal is performed based on first light emission of the next set of light emissions. Accordingly, the power consumption of the sensor module 10 can be reduced by lowering the clock frequency of the CPU 133 while maintaining the measurement cycle of the sensor module 10.

As described above, each time the light receiving element 121a receives light having the first central wavelength $\lambda 1$ from the light emitting element 111a, the controller 13 performs the moving average process for averaging, with respect to the first central wavelength $\lambda 1$, a signal output from the light receiver 12. Further, each time the light receiving element 121a receives light having the second central wavelength $\lambda 2$ from the light emitting element 112a, the controller 13 performs the moving average process for averaging, with respect to the second central wavelength $\lambda 2$, a signal output from the light receiver 12. Accordingly, noise of the signals output from the light receiver 12 can be reduced, allowing the controller 13 to estimate biological information with higher accuracy.

Figure 9A:
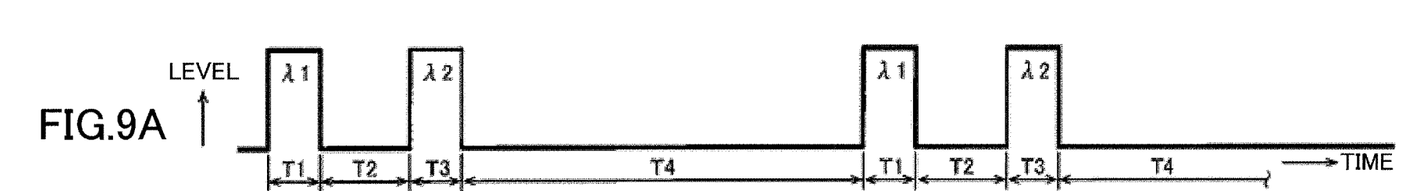
FIGS. 9A through 9C are timing diagrams illustrating another biological information estimating operation according to the embodiment.
Figure 9B:
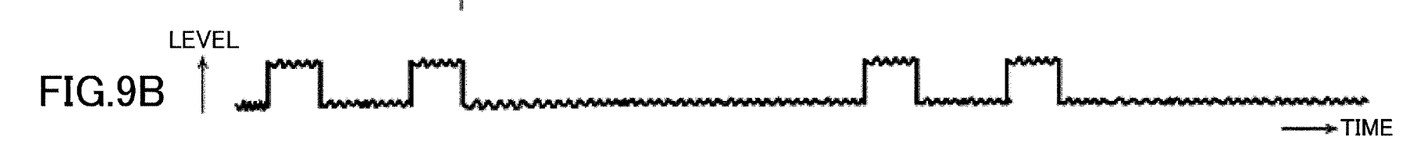
Figure 9C:
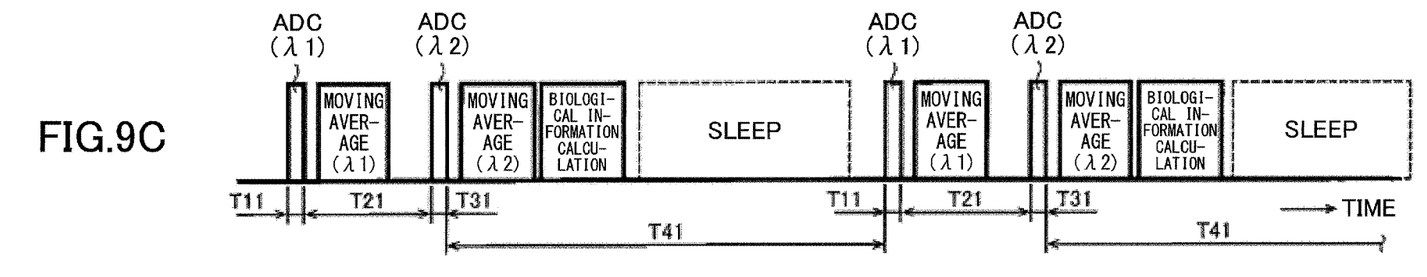

FIGS. 9A through 9C are timing diagrams illustrating another biological information estimating operation according to the present embodiment. FIG. 9A represents the level of timing signals (light emitting signals) transmitted from the controller to the light emitter. FIG. 9B represents the level of amplified light reception signals output from the light receiver. FIG. 9C represents timings at which the controller performs processes. In each of the timing diagrams illustrated in FIGS. 9A through 9C, the horizontal axis represents time.

In the biological information estimating operation illustrated in FIGS. 9A through 9C, after the estimation process is performed by the CPU 133 in the processing period of time T41 set in correspondence with the second non-light-emission period of time T4, the controller 13 enters sleep mode that reduces the supply of power to the CPU 133. The biological information estimating operation illustrated in FIGS. 9A through 9C differs in this regard from the biological information estimating operation described above with reference to FIGS. 7A through 7D. Other configurations are the same as those of the biological information estimating operation described above with reference to FIGS. 7A through 7D.

Accordingly, because the processing period of time T41 is set sufficiently longer than the processing period of time T21, the controller 13 can secure time to enter sleep mode that reduces the supply of power to the CPU 133 in the processing period of time T41. Therefore, it is possible to reduce the power consumption of the sensor module 10 without necessarily lowering the clock frequency of the CPU 133. Further, even when the clock frequency of the CPU 133 is lowered, the measurement cycle can be maintained. Thus, the power consumption of the sensor module 10 can be further reduced while maintaining the accuracy of measurement.

Further, the biological information display system 1 according to the present embodiment includes the sensor module 10 described above with reference to FIG. 1 through FIG. 9C. Thus, the power consumption of the sensor module 10 can be reduced by lowering the clock frequency of the CPU 133. Further, the biological information display system 1 is able to display, on the display unit 21, biological information estimated by the controller 13 while reducing the power consumption of the sensor module 10. In addition, the biological information display system 1 is able to estimate, as biological information, at least one selected from a group consisting of changes in blood hemoglobin, changes in blood oxygen level, and a pulse rate, while reducing the power consumption of the sensor module 10.

Although the embodiments and application examples thereof have been described above, the present invention is not limited thereto. For example, addition, deletion, or a design change of components, or combinations of features of the above embodiments may be appropriately made by those skilled in the art without departing from the gist of the present invention.

For example, in the above-described sensor module 10, the controller 13 includes the vital estimating unit 133a that estimates biological information, and controls the operation of the light emitter 11 by outputting a control signal to the light emitter 11; however, the present invention is not limited thereto. Any component other than the controller 13 may control the operation of the light emitter 11, and the controller 13 may perform the estimation process and other processes (such as the moving average process) in response to a signal output from the light receiver 12 being input.

In the sensor module 10 according to the present embodiment, the moving average process is performed in the processing period of time T21 (T22) set in correspondence with the first non-light-emission period of time T2, and standby time during which no process is performed by the CPU 133 is provided after the moving average process until the next AD conversion is started. The controller 13 may enter sleep mode of the CPU 133 during the standby time. As a result, the power consumption of the sensor module can be further reduced. It should be noted that if the moving average process is not performed in a processing period of time set in correspondence with a first non-light-emission period of time, or if the moving average process is performed by a processing unit other than the CPU 133, the entire processing period of time set in correspondence with the first non-light-emission period of time is standby time. In such a case, the controller 13 may enter sleep mode of the CPU 133 during the standby time.

If light is emitted three or more times in a set of light emissions, the set of light emissions include two or more first non-light-emission periods of time. In this case, the first non-light-emission periods of time may have the same length or different lengths. If a plurality of first non-light-emission periods of time have different lengths, the length of a second non-light-emission period of time is preferably set longer than the longest period of time of the plurality of first non-light-emission periods of time.

According to at least one embodiment, a sensor module includes a light emitter configured to emit light beams including near-infrared light beams towards a subject, a light receiver configured to receive light beams that have passed through the subject, and a controller configured to estimate biological information based on signals output from the light receiver. The light emitter includes a plurality of first light emitting elements disposed spaced apart from each other and configured to emit near-infrared light beams having central wavelengths different from each other. The light receiver includes a light receiving element that is disposed to receive the near-infrared light beams emitted from the plurality of first light emitting elements and that is sensitive to the near-infrared light beams. The light emitter produces sets of light emissions by causing the plurality of first light emitting elements to sequentially and intermittently emit the near-infrared light beams, and, in given two consecutive sets of light emissions produced by the light emitter, a second non-light-emission period of time is longer than a first non-light-emission period of time, the first non-light-emission period of time being a non-light-emission period of time occurring between two consecutive light emission periods of time in each of the given two consecutive sets of light emissions, and the second non-light-emission period of time being a non-light-emission period of time occurring between a light emission period of time that occurs last in a first set of light emissions of the given two consecutive sets of light emissions and a light emission period of time that occurs first in a latter set of light emissions of the given two consecutive sets of light emissions. The controller estimates the biological information in a processing period of time that is set in correspondence with the second non-light-emission period of time.

In the above-described sensor module, the controller may include a central processing unit configured to perform an estimation process for estimating the biological information, and after the estimation process is performed by the central processing unit, the controller may enter sleep mode that reduces supply of power to the central processing unit, in the processing period of time that is set in correspondence with the second non-light-emission period of time. Because the second non-light-emission period of time is longer than the first non-light-emission period of time, the processing period of time set in correspondence with the second non-light emission period of time is set longer than a processing period of time set in correspondence with the first non-light emission period of time. Therefore, the controller can secure time to enter sleep mode that reduces that reduces supply of power to the central processing unit after the estimation process is performed by the central processing unit. Accordingly, it becomes possible to reduce the power consumption of the sensor module without necessarily lowering the clock frequency of the controller. Further, the power consumption of the sensor module can be further reduced by lowering the clock frequency of the controller.

The controller may include a central processing unit configured to perform an estimation process for estimating the biological information, and the controller may enter sleep mode that reduces supply of power to the central processing unit, in at least a part of another processing period of time that is set in correspondence with the first non-light-emission period of time. As described above, the central processing unit performs the estimation process in the second non-light-emission period of time. Thus, the central processing unit is not required to be actively operated in the entire processing period of time set in correspondence with the first non-light-emission period of time if a moving average process is not performed. If the moving average process is performed, the central processing unit is not required to be actively operated in a period of time after the moving average process is performed in the processing period of time set in correspondence with the first non-light-emission period of time. Accordingly, the controller may enter sleep mode in the processing period of time set in correspondence with the first non-light-emission period of time. As a result, the power consumption of the sensor module can be further reduced.

In the above-described sensor module, the controller may perform a moving average process for averaging a signal output from the light receiver on a per-same-central-wavelength basis, each time the light receiving element receives a near-infrared light beam emitted from a first light emitting element of the plurality of first light emitting elements. Thus, the moving average process for averaging a signal output from the light receiver on a per-same-central-wavelength basis is performed each time the light receiver receives a near-infrared light beam. Accordingly, noise of the signals output from the light receiver can be reduced, allowing the controller to estimate biological information with higher accuracy.

In the above-described sensor module, the light emitter may further include a plurality of second light emitting elements configured to emit near-infrared light beams having central wavelengths that are same as the central wavelengths of the near-infrared light beams emitted from the plurality of respective first light emitting elements. Timings of light emitting elements, of the plurality of first light emitting elements and of the plurality of second light emitting elements, emitting near-infrared light beams having a same central wavelength may be synchronized with each other. As described, the plurality of first light emitting elements and the plurality of second light emitting elements having the same central wavelengths are provided. Further, timings at which the plurality of first light emitting elements and the plurality of second light emitting elements having a same central wavelength emit near-infrared light beams are synchronized with each other. Therefore, the light receiver can obtained higher detection sensitivity. Accordingly, the controller can estimate biological information with higher precision, even if an artery is located deeper below the skin of the subject, for example.

A biological information display system according to at least one embodiment may include the above-described sensor module, and a display unit configured to display the biological information estimated by the controller.

Because the biological information display system includes the above-described sensor module, it is possible to reduce the power consumption of the sensor module by decreasing the clock frequency of the controller. Further, the biological information display system can cause the display unit to display the biological information estimated by the controller.

According to the above-described biological information display system, the controller may estimate, as the biological information, at least one selected from a group consisting of a change in blood hemoglobin, a change in oxygen level, and a pulse rate. Accordingly, the biological information display system can estimate, as the biological information, at least one selected from a group consisting of a change in blood hemoglobin, a change in blood oxygen level, and a pulse rate, while reducing the power consumption of the sensor module.

According to at least one embodiment, it is possible to provide a sensor module and a biological information display system that reduce power consumption.

Further, the present invention is not limited to these embodiments, but various variations and modifications may be made without departing from the scope of the present invention.

What is claimed is:

1. A sensor module comprising:
a light emitter configured to emit light beams including near-infrared light beams towards a subject;
a light receiver configured to receive light beams that have passed through the subject; and
a controller configured to estimate biological information based on signals output from the light receiver,
wherein the light emitter includes a plurality of first light emitting elements disposed spaced apart from each other and configured to emit near-infrared light beams having central wavelengths different from each other,
wherein the light receiver includes a light receiving element that is disposed to receive the near-infrared light beams emitted from the plurality of first light emitting elements and that is sensitive to the near-infrared light beams,
wherein the light emitter produces sets of light emissions by causing the plurality of first light emitting elements to sequentially and intermittently emit the near-infrared light beams, and, in given two consecutive sets of light emissions produced by the light emitter, a second non-light-emission period of time is longer than a first non-light-emission period of time, the first non-light-emission period of time being a non-light-emission period of time occurring between two consecutive light emission periods of time in each of the given two consecutive sets of light emissions, and the second non-light-emission period of time being a non-light-emission period of time occurring between a light emission period of time that occurs last in a first set of light emissions of the given two consecutive sets of light emissions and a light emission period of time that occurs first in a latter set of light emissions of the given two consecutive sets of light emissions, and
wherein the controller estimates the biological information in a processing period of time that is set in correspondence with the second non-light-emission period of time.

2. The sensor module according to claim 1, wherein the controller includes a central processing unit configured to perform an estimation process for estimating the biological information, and after the estimation process is performed by the central processing unit, the controller enters sleep mode that reduces supply of power to the central processing unit, in the processing period of time that is set in correspondence with the second non-light-emission period of time.

3. The sensor module according to claim 1, wherein the controller includes a central processing unit configured to perform an estimation process for estimating the biological information, and enters sleep mode that reduces supply of power to the central processing unit, in at least a part of another processing period of time that is set in correspondence with the first non-light-emission period of time.

4. The sensor module according to claim 1, wherein the controller performs a moving average process for averaging a signal output from the light receiver on a per-same-central-wavelength basis, each time the light receiving element receives a near-infrared light beam emitted from a first light emitting element of the plurality of first light emitting elements.

5. The sensor module according to claim 1, wherein the light emitter further includes a plurality of second light emitting elements configured to emit near-infrared light beams having central wavelengths that are same as the central wavelengths of the near-infrared light beams emitted from the plurality of respective first light emitting elements, and
wherein timings of light emitting elements, of the plurality of first light emitting elements and of the plurality of second light emitting elements, emitting near-infrared light beams having a same central wavelength are synchronized with each other.

6. A biological information display system comprising:
the sensor module according to claim 1; and
a display unit configured to display the biological information estimated by the controller.

7. The biological information display system according to claim 6, wherein the controller estimates, as the biological information, at least one selected from a group consisting of a change in blood hemoglobin, a change in blood oxygen level, and a pulse rate.

* * * * *